US011413349B2

(12) United States Patent
Oyarzún Ampuero et al.

(10) Patent No.: US 11,413,349 B2
(45) Date of Patent: Aug. 16, 2022

(54) GREEN METHODOLOGY TO CREATE POLYMERIC NANOCARRIERS CONTAINING HYDROPHILIC LOW MOLECULAR-WEIGHT DRUGS AND PROVIDING A VERY HIGH DRUG LOADING AND A VERY HIGH PROLONGED RELEASE

(71) Applicants: UNIVERSIDAD DE CHILE, Santiago (CL); UNIVERSIDAD AUSTRAL DE CHILE, Valdivia (CL)

(72) Inventors: Felipe Andrés Oyarzún Ampuero, Santiago (CL); Ignacio Moreno Villoslada, Valdivia (CL); Maria Gabriela Villamizar Sarmiento, Santiago (CL); Elton Fabian Molina Soto, Valdivia (CL)

(73) Assignees: UNIVERSIDAD DE CHILE, Santiago (CL); UNIVERSIDAD AUSTRAL DE CHILE, Valdivia (CL)

(*) Notice: Subject to any disclaimer, the term of this patent is extended or adjusted under 35 U.S.C. 154(b) by 60 days.

(21) Appl. No.: 16/888,438

(22) Filed: May 29, 2020

(65) Prior Publication Data

US 2020/0376127 A1 Dec. 3, 2020

Related U.S. Application Data

(60) Provisional application No. 62/854,168, filed on May 29, 2019.

(51) Int. Cl.
*A61K 47/34* (2017.01)
*A61K 47/38* (2006.01)
(Continued)

(52) U.S. Cl.
CPC .............. *A61K 47/34* (2013.01); *A61K 47/38* (2013.01); *A61K 45/06* (2013.01); *B82Y 5/00* (2013.01)

(58) Field of Classification Search
CPC ........ A61K 47/34; A61K 47/38; A61K 45/06; A61K 9/19; A61K 9/5161; A61K 9/5138;
(Continued)

(56) References Cited

PUBLICATIONS

Villamizar-Sarmiento et al, A New Methodology to Create Polymeric Nanocarriers Containing Hydrophilic Low Molecular Weight Drugs: A Green Strategy Providing Very High Drug Loading, Mol. Pharmaceutics, pp. 2892-2901 (Year: 2019).*

(Continued)

*Primary Examiner* — Carlos A Azpuru
(74) *Attorney, Agent, or Firm* — Procopio, Cory, Hargreaves & Savitch LLP

(57) ABSTRACT

In one aspect, provided herein is a nanocarrier composition for formulating a hydrophilic and aromatic low molecular-weight drug (HALMD), the composition comprising: an aromatic polymer; and a hydrophilic and aromatic low molecular-weight drug (HALMD);
wherein the aromatic polymer has a positive or negative charge or is a zwitterion, and the hydrophilic and aromatic low molecular-weight drug (HALMD) has an opposing positive or negative charge or is a zwitterion; and wherein the composition has a size of between 50-400 nm and optionally, a zeta potential of from +100 to −100 mV. A method for preparing the nanocarrier composition, as well as pharmaceutical compositions and therapeutic uses thereof, are also disclosed.

8 Claims, 6 Drawing Sheets

(51) Int. Cl.
*A61K 45/06* (2006.01)
*B82Y 5/00* (2011.01)

(58) Field of Classification Search
CPC .............. A61K 31/135; A61K 31/4402; A61K 31/4706; A61K 31/5415; A61K 31/55; B82Y 5/00
See application file for complete search history.

(56) References Cited

PUBLICATIONS

Villamizar-Sarmiento, M.G., et al., A New Method to Create Polymeric Nanocarriers Containing Hydrophilic Low Molecular-Weight Drugs: A Green Strategy Providing a Very High Drug Loading, Mol, Pharmaceutics, 2019. 16, pp. 2892-2901.

* cited by examiner

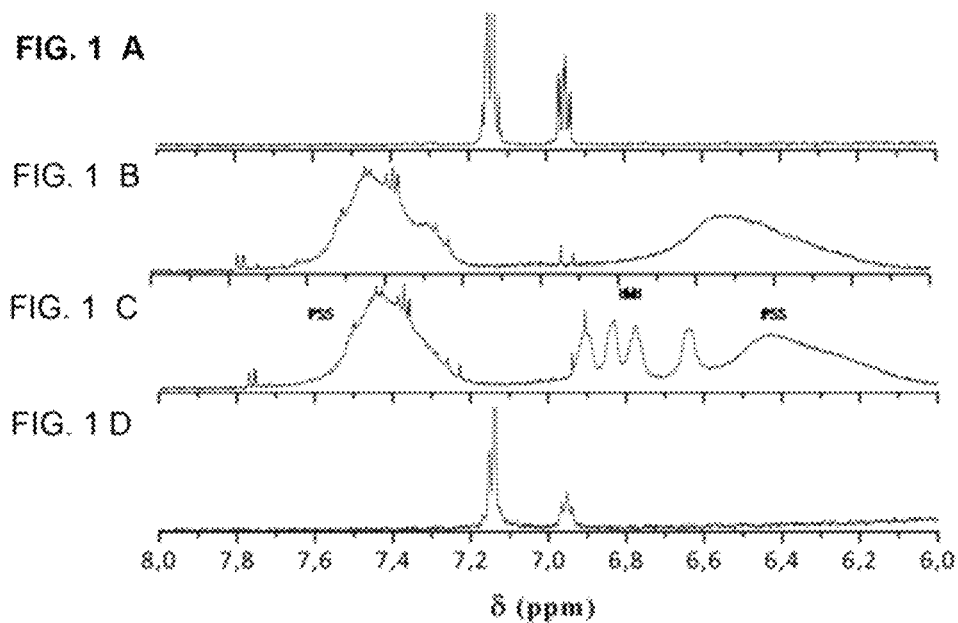
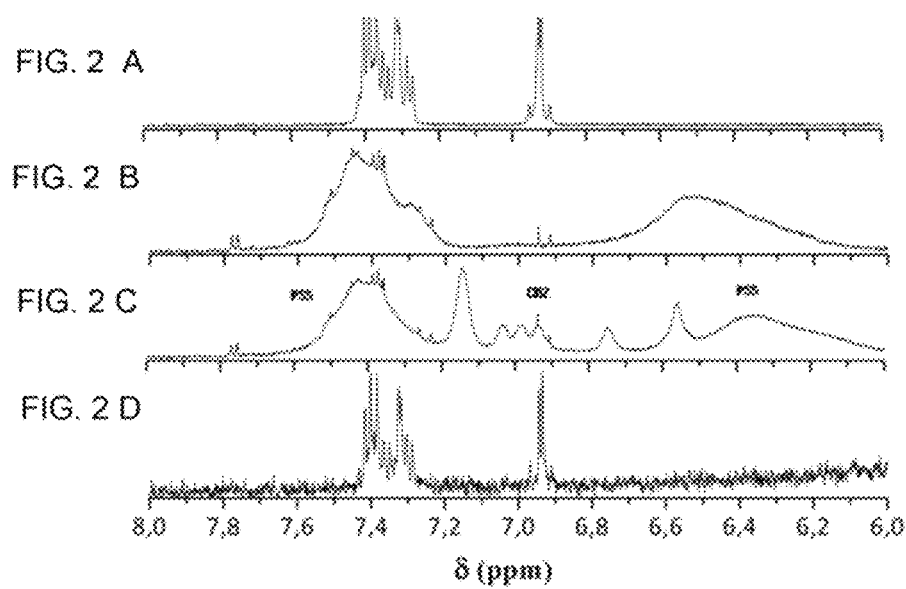

FIG. 3 A
FIG. 3 B
FIG. 3 C
FIG. 3 D
FIG. 3 E
FIG. 3 F
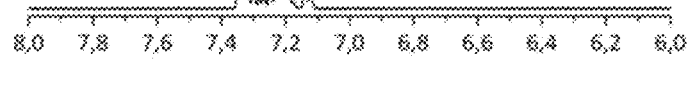
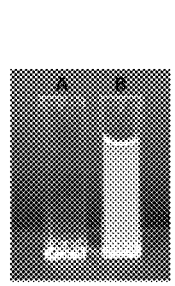
FIG. 4 A   FIG. 4 B
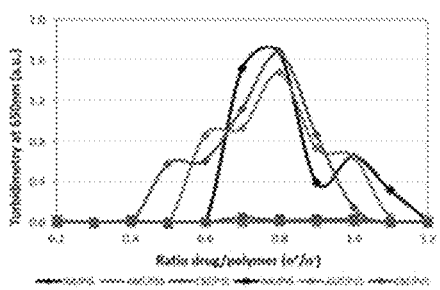
FIG. 4 C
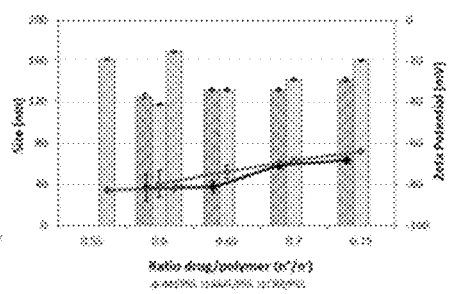
FIG. 4 D

GREEN METHODOLOGY TO CREATE POLYMERIC NANOCARRIERS CONTAINING HYDROPHILIC LOW MOLECULAR-WEIGHT DRUGS AND PROVIDING A VERY HIGH DRUG LOADING AND A VERY HIGH PROLONGED RELEASE

CROSS-REFERENCE TO RELATED APPLICATIONS

This application is a U.S. Provisional Application No. 62/854,168 filed May 29, 2019, the contents of which are incorporated herein by reference.

FIELD OF THE INVENTION

The present invention relates generally to the field of formulation and drug delivery. More particularly, the present invention relates to a nanocarrier composition for formulating a hydrophilic and aromatic low molecular-weight drug (HALMD), and a method of obtaining the composition.

BACKGROUND

To date, a large number of available drugs are low molecular-weight (<900 Da) compounds or compositions. Interestingly, most are hydrophilic, ionizable and have aromatic functional groups. These drugs belong to different therapeutic groups and are targeted towards several acute and chronic pathologies, including pain, inflammation, depression, hypertension, allergy, diabetes, and infections, among others. Importantly, these hydrophilic, aromatic and low molecular-weight drugs (HALMD) are easier to synthesize than others (i.e. large molecular-weight drugs and/or hydrophobic drugs) and can also be customized towards desired targets, for example, by using quantitative structure-activity relationship (QSAR) predictions.

Considering the physicochemical characteristics of HALMD, their chemical entrapment in drug delivery systems using non-covalent interactions to provide controlled release formulations represents an unsolved challenge for the scientific community. This is due to the very low capacity of HALMD to interact positively with excipients and the very fast release of these drugs upon exposure to biological media. For example, there are a large number of hydrogel formulations that provide efficient entrapment and prolonged release of macromolecules or hydrophobic drugs. Conversely, only a few studies researching the entrapment and prolonged release of HALMD are found in the literature. In one interesting study, Chen et al (International Journal of Molecular Sciences, 2018, 19, (5), 1373.) proposed the encapsulation of doxorubicin in poly(N-isopropylacrylamide)-based thermosensitive hydrogel, and an initial 40% of drug release was shown.

Interesting examples of HALMD are tricyclic molecules that show therapeutic effect in the nervous system. Among tricyclic drugs, imipramine (IMI), amitriptyline (AMT) and cyclobenzaprine (CBZ) are common protagonists. These molecules are hydrophilic when exposed to biological media at physiological pH due to the ionization of the amine functional groups with pKa 8.4-9.4. Imipramine and amitriptyline act as antidepressants, blocking the reuptake of neurotransmitters (norepinephrine and serotonin). Cyclobenzaprine belongs to a class of drugs called musculoskeletal relaxants. The exact mechanism of action of this molecule has not been fully determined, but it seems to act by influencing both gamma and alpha motor neurons. Among issues with the use of these drugs and other tricyclic molecules are important side effects such as sedation, drowsiness, blurred vision, cardiotoxicity, delirium, and coma. While the presence of these side effects is attributable to unspecific effects of the drugs, their magnitude is thought to be due to the uncontrolled release and fast systemic absorption from the pharmaceutical dosage form (80-90% of absorption after 2 hours of administration). In this respect, Tomida et al (Chemical & Pharmaceutical Bulletin, 1993, 41, 8:1475-1477) studied the drug release of imipramine from calcium-alginate gel beads and showed a burst release of ≈80% in few hours (1-2 h). Similar results were found by Ahnfelt et al (J Control Release, 2018 292: 235-247) when studying the release of AMT (achieving >80% of release within the first stage of the experiment) from polyvinyl alcohol-based beads. In these studies, the results indicate that the release rate was determined by fast diffusion of the drug through the polymeric network.

The use of nanotechnology has been of great interest for the pharmaceutical industry in recent decades. Especially, polymeric nanoparticles (NPs) have taken a step forward in the development of new drug delivery systems, offering great versatility in synthesis methods and integrating several materials that directly impact on the physicochemical properties of the desired systems. A very promising strategy to generate polymeric NPs containing hydrophilic drugs consists of simply mixing two aqueous solutions containing oppositely charged macromolecules at room temperature, wherein one solution contains the drug and the other solution contains the polymer. In this case, the entrapment of the drug is governed by positive ionic interactions between the macromolecular components. As a result, this strategy is limited to the use of large polyionic drugs. Interestingly, other more sophisticated strategies to encapsulate hydrophilic low molecular-weight drugs into nanoparticles have been published, including freezing an inner phase of a multiple emulsion containing polymeric NPs, self-assembly of NPs comprising chemically-modified polymers, and synthesis of oxidized cellulose nanocrystals/chitosan oligosaccharide grafted cellulose nanocrystals. Unfortunately, very low drug loading and/or fast drug release were seen in all cases.

In light of the deficiencies of the art, a new, environmentally friendly and highly efficient methodology to attach HALMD non-covalently to hydrophilic aromatic polymers to create nanocarriers and a nanocarrier composition have been devised for delivering a hydrophilic and aromatic low molecular-weight drug (HALMD). The nanocarrier composition of the present invention comprises an aromatic polymer and a hydrophilic and aromatic low molecular-weight drug (HALMD).

SUMMARY OF THE INVENTION

The present invention provides a nanocarrier composition for formulating a hydrophilic and aromatic low molecular-weight drug (HALMD), the composition comprising an aromatic polymer and a hydrophilic and aromatic low molecular-weight drug (HALMD), wherein the aromatic polymer and the hydrophilic and aromatic low molecular-weight drug (HALMD) have opposite electric charges. The composition has a size range of between 50-400 nm, and optionally, a zeta potential from +100 to −100 mV.

Also described is a method for preparing a nanocarrier composition for formulating a hydrophilic and aromatic low molecular-weight drug (HALMD), comprising mixing at room temperature an aqueous solution of an aromatic polymer with an aqueous solution of a hydrophilic and aromatic low molecular-weight drug (HALMD); wherein the aqueous solution of the aromatic polymer and the aqueous solution of the hydrophilic and aromatic low molecular-weight drug (HALMD) having opposite electric charges; wherein the final apparent concentration is between 0.1 and 1.2; and wherein both aqueous solutions are at pH equal to 7.

BRIEF DESCRIPTION OF THE DRAWINGS

FIG. 1 shows 1H-NMR aromatic region spectra (500 MHz) in $D_2O$ at pH 7 of: imipramine (IMI) $1\times10^{-3}$ M in the absence of any polymer (FIG. 1A), poly(sodium 4-styrene-sulfonate) (PSS) $1\times10^{-2}$ M (FIG. 1B), IMI $1\times10^{-3}$ M in the presence of PSS $1\times10^{-2}$ M (FIG. 1C) and IMI in the presence of polyvinylsulphonate (PVS) $1\times10^{-2}$ M (FIG. 1D).

FIG. 2 shows 1H-NMR aromatic region spectrum (500 MHz) in $D_2O$ at pH 7 of: cyclobenzaprine (CBZ) $1\times10^{-3}$ M in the absence of any polymer (FIG. 2A), PSS $1\times10^{-2}$ M (FIG. 2B), CBZ $1\times10^{-3}$ M in the presence of PSS $1\times10^{-2}$ M (FIG. 2C) and CBZ in the presence of PVS $1\times10^{-2}$ M (FIG. 2D).

FIG. 3 shows 1H-NMR aromatic region spectrum (400 MHz) in $D_2O$ of amitriptyline (AMI) 100 mM (FIG. 3A), AMI 50 mM (FIG. 3B), AMI 30 mM (FIG. 3C), AMI 20 mM (FIG. 3D), AMI 10 mM (FIG. 3E), AMI 1 mM (FIG. 3F).

FIG. 4 shows optical images of the AMT/PVS (FIG. 4A) and AMT/PSS (FIG. 4B). Turbidimetric measurements of drugs/PSS (•) and drugs/PVS (■) formulations are shown in FIG. 4C. Apparent hydrodynamic diameter (bars) and zeta potential (lines) for drugs/PSS formulations are shown in FIG. 4D (Mean±SD; n=3).

DETAILED DESCRIPTION OF THE INVENTION

Figure 5:
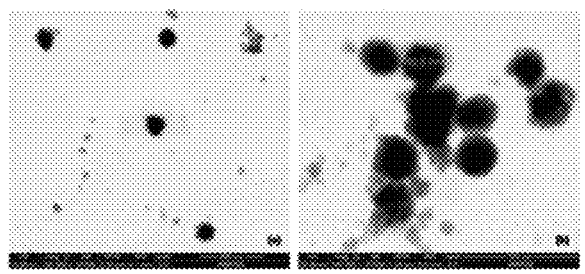
FIG. 5 shows scanning transmission electron microscopy images of AMT/PSS (n+/n− 0.7) 130000× (FIG. 5A), 240000× (FIG. 5B).

To the date, a large number of active molecules are hydrophilic and aromatic low molecular-weight drugs (HALMD). Unfortunately, the low capacity of these molecules to interact with excipients, and the fast release when a formulation containing them when exposed to biological media, jeopardizes the effectiveness of drug delivery systems due to non-covalent interactions.

The solution proposed by way of the present invention consists of a nanocarrier composition for the formulation of a HALMD, and a method of obtaining the composition. The composition comprises, simply, an aromatic polymer and a HALMD. The method comprises the simple mixture of two aqueous solutions with formation of the composition being based on ionic affinity and stabilization by aromatic-aromatic interactions. The formation of the nanoparticles (NPs) prepared through this environmentally friendly and simple methodology is critically dependent on the presence of the aromatic group in the polymer. Interestingly, stopped-flow and diafiltration experiments demonstrated that kinetic rather than thermodynamic interactions governed the systems. Obtained NPs show spheroidal shape, a size range of 50 to 400 nm and a zeta potential of +100 to −100 mV. Importantly, in addition to high drug association efficiencies (≥90%), the formed nanocarriers showed drug loading values not seen with other formulations comprising HALMD, reaching ≈50%. A very prolonged drug release was also seen with the formulation of the invention. Finally, the NPs were transformable into a reconstitutable dry powder without losing their original characteristics.

Thus, according to one aspect, the present invention resides in a nanocarrier composition for formulating a hydrophilic and aromatic low molecular-weight drug (HALMD), the composition comprising: an aromatic polymer; and a hydrophilic and aromatic low molecular-weight drug (HALMD), wherein the aromatic polymer has a positive or negative charge or is a zwitterion, and the hydrophilic and aromatic low molecular-weight drug (HALMD) has an opposing positive or negative charge or is a zwitterion; wherein the composition has a size of between 50-400 nm, and, optionally, a zeta potential from +100 to −100 mV.

In one embodiment, the aromatic polymer and the HALMD are present in the composition in a concentration such that the final apparent concentration is defined according the following formula:

$$[\text{final apparent concentration}] = \frac{n+}{n-}$$

wherein n+ is the molar concentration of a cationic aqueous solution and n− is the molar concentration of an anionic aqueous solution.

Aromatic polymers wholly or partially include benzene rings and/or pseudoaromatic heterocycles and have been widely used in high-performance or functional materials, Aromatic polymers include (1) linear or branched aromatics; and (2) linear or branched polymers with aromatic units in the chain. The first group includes polystyrene and derivatives, polyvinyl pyridine and polyvinyl carbazole while the second group covers polyesters, polyamides, polyethers, polysulfides, polysulfoxides and polysulfones, polyhydrocarbons, polyimides, and ladder polymers. For the present invention, linear polyvinyl aromatic polymers are preferred. Examples of suitable aromatic polymers include poly(sodium 4-styrenesulfonate) (PSS) and hypromellose phthalate. PSS is approved by the US Food and Drug Administration for the treatment of hyperkalemia, and several researchers aim to use PSS as a pharmaceutical coating material due to its excellent biocompatibility, non-cytotoxicity, non-immunogenic properties and antimicrobial activity.

Considering that many drugs are hydrophilic, low molecular-weight molecules including ionizable groups and aromatic rings (antihistaminic, antibiotics, antitumoral, antiarrhythmic, antidepressants, antidiabetic, antipsychotic, antibacterial, antihypertensive, nonsteroidal anti-inflammatory, and others), it will be appreciated that the nanoparticle composition of the present invention is applicable to the formulation and therapeutic delivery of a large number of drugs. Examples of specific hydrophilic and aromatic low molecular-weight drugs are tricyclic drugs and cyclobenzaprine (CBZ). Tricyclic drugs are typically antidepressants such as imipramine (IMI), amitriptyline (AMT), amoxapine, desipramine, doxepin, nortriptyline, protriptyline and trimipramine. Other examples of HALMD are atenolol, metoprolol, propranolol, amlodipine, doxorubicin, paroxetine, venlafaxine and levodopa. Other preferable HALMD are antihistaminic drugs including carbinoxamine, clemastine, dimenhydrinate, diphenhydramine, doxylamine, pyrilamine, tripelennamine, chlorpyramine, chlorpheniramine, brompheniramine, cyproheptadine, hydroxyzine, ciclizine, meclizine, promethazine, acrivastine, cetirizine, terfenadine, astemizole, levocabastine, loratadine, azatadine, phenindamine, diphenylpyraline, ebastine, levocetirizine, fexofenadine, desloratadine, tecastemizole. Another preferable HALDM are antiviral or antimalarial drugs including chloroquine, hydroxychloroquine, amodiaquine and mefloquine.

It will be appreciated that the term "hydrophilic and aromatic low molecular-weight drug" defines a compound having a therapeutic effect. The compound is hydrophilic and aromatic. Low molecular weight typically refers to small molecules that are easily able to enter cells. An upper weight limit for small molecules is generally thought to be e.g. 1500 Daltons, preferably 900 Daltons, more preferably 600 Daltons. Of course, it will be appreciated that the molecular weight of the HALMD needs to be within the total size of the formulation, namely within a total composition size of between about 50 and about 400 nm. In a particular embodiment, the HALMD may be positively charged IMI, AMT or CBZ, while the polymer may be negatively charged poly(sodium 4-styrenesulfonate) (PSS) or hypromellose phthalate.

While the essential agents of the composition of the present invention are a HALMD, as the active ingredient, and an aromatic polymer, it will be appreciated that the composition may be formulated for therapeutic administration. As such, the present invention also encompasses a pharmaceutical composition or medicament comprising a nanocarrier composition as described herein and, optionally, one or more physiologically or pharmaceutically acceptable carriers, excipients and/or diluents.

The pharmaceutical composition or medicament of the present invention may be used in a method of treatment in which a therapeutically effective amount of a pharmaceutically or physiologically acceptable composition comprising a nanoparticle composition as described herein is administered to a subject in need thereof. Expressed in another way, also encompassed is use of a pharmaceutically or physiologically acceptable composition comprising a nanoparticle composition as described herein for therapeutic use in or on a human or animal. It will be appreciated that the therapeutic use will depend on the therapeutic application of the HALMD. For example, where the HALMD is a tricyclic antidepressant, the therapeutic use will be for the treatment of depression and associated and related disorders. Similarly, where the HAMLD is cyclobenzaprine, the therapeutic use will be for the treatment of conditions caused by muscle spasm due to acute musculoskeletal conditions, such as fibromyalgia, low back pain, and neck pain.

The term "one or more physiologically or pharmaceutically acceptable carriers, excipients and/or diluents" as used herein is intended to include any and all solvents, dispersion media, coatings, antibacterial and antifungal agents, isotonic and absorption delaying agents, and the like, compatible with administration to humans or other vertebrate hosts. Typically, a pharmaceutically acceptable diluent, excipient, and/or carrier is a diluent, excipient, and/or carrier approved by a regulatory agency of a Federal, a state government, or other regulatory agency, or listed in the US and/or European Pharmacopeia or other generally recognized pharmacopeia for use in animals, including humans as well as non-human mammals.

The term "diluent, excipient, and/or carrier" refers to a diluent, adjuvant, excipient, or vehicle with which the pharmaceutical composition is administered. Such pharmaceutical diluent, excipient, and/or carriers may be sterile liquids, such as water and oils, including those of petroleum, animal, vegetable or synthetic origin. Water, saline solutions and aqueous dextrose and glycerol solutions may be employed as liquid diluents, excipients, and/or carriers, particularly for injectable solutions. Suitable pharmaceutical diluents and/or excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, may also contain minor amounts of wetting, bulking, emulsifying agents, or pH buffering agents.

The pharmaceutical compositions of the present invention may take the form of solutions, suspensions, emulsion, sustained release formulations and the like. Examples of suitable pharmaceutical diluents, excipients, and/or carriers are described in "Remington's Pharmaceutical Sciences" by E. W. Martin. The formulation should suit the mode of administration. The appropriate diluent, excipient, and/or carrier will be evident to those skilled in the art and will depend in large part upon the route of administration.

As used herein, an "effective amount" of nanocarrier composition as described herein refers to the amount necessary to elicit the desired biological response. As will be appreciated by those of ordinary skill in this art, the effective amount of a nanoparticle containing the therapeutic agent may vary depending on such factors as the desired biological endpoint, the drug to be delivered, the target tissue, the route of administration, etc. Additional factors which may be taken into account include disease severity; age, weight and gender of the patient being treated; diet, time and frequency of administration; drug combinations; reaction sensitivities; and tolerance/response to therapy.

Medicaments described herein may be provided as a kit which comprises at least one container and a package insert. The container contains at least one dose of a medicament comprising a composition as described herein. The package insert, or label, comprises instructions for treating a patient using the medicaments as described herein. The kit may further comprise other materials that may be useful in administering the medicaments, such as diluents, filters, IV bags and lines, needles and syringes.

In another aspect, the present invention provides a method for preparing a nanocarrier composition for formulating a hydrophilic and aromatic low molecular-weight drug (HALMD) as described herein above. The method comprises: mixing at room temperature at least an aqueous solution of an aromatic polymer with at least an aqueous solution of a hydrophilic and aromatic low molecular-weight drug (HALMD) in a concentration such that the final apparent concentration is defined according the following formula:

$$[\text{final apparent concentration}] = \frac{n+}{n-}$$

wherein n+ is the molar concentration of a cationic aqueous solution and n− is the molar concentration of an anionic aqueous solution. The aqueous solutions are adjusted to a pH between 4 to 9, preferably between 5 and 8, more preferably 7; and the final apparent concentration is between 0.1 and 1.6.

In one embodiment, the pH may be adjusted with acid and/or base, preferably with hydrochloric acid and/or sodium hydroxide.

In another embodiment, the aqueous solution of the aromatic polymer may be an anionic aqueous solution, wherein the concentration of the aqueous solution ranges from $1\times10^{-3}$ to $4\times10^{-3}$ Molar, preferably $1.7\times10^{-3}$ Molar; and the aqueous solution of the hydrophilic and aromatic low molecular-weight drug may be a cationic aqueous solution.

In another embodiment, the nanocarrier composition has drug a loading value from 30 to 100%, preferably 50% to 70%.

The following examples are provided to illustrate certain embodiments of the invention and they are not intended to limit the invention in any way.

EXAMPLES

Example 1

Physicochemical Characterization of Nanocarriers Containing HALMD

Drug/polymer formulations containing amitriptyline (AMT) and either poly(sodium 4-styrenesulfonate) (PSS) or polyvinylsulphonate (PVS) were synthesized by simply mixing two aqueous solutions in a ratio such that n+/n−=0.1 to 1.6, at room temperature. The presence and dispersion of particles in aqueous medium was initially analyzed using standard turbidimetry methodology in a spectrophotometer. Absorbance of the formulations was measured at a wavelength where neither of the two compounds (drug and polymer) absorbed ($\lambda$=650 nm).

The hydrodynamic diameter and zeta potential of the formulations were determined by Dynamic Light Scattering (DLS) and laser Doppler anemometry (LDA) using standard protocols.

The morphological characterization was carried out in a Scanning Transmission Electron Microscope (STEM). STEM images were obtained by sticking a droplet (20 µL) of the formulation to a copper grid (200 mesh, covered with Formvar®) for 2 min, then removing the droplet, washing the grid and removing the droplet. Subsequently, the sample was stained with a solution of 1% (w/v) phosphotungstic acid. Finally, the grid was dried at room temperature for at least 1 hour before being analyzed.

The stability of the formulations was evaluated as a function of time in terms of hydrodynamic diameter and zeta potential, and under variation in NaCl concentration, pH, and temperature. The concentration of NaCl in the medium was controlled with an automatic titrator. For pH variations, HCl (0.25-0.01 M) and NaOH (0.25-0.01 M) solutions were selected and controlled with the automatic titrator. The temperature of the samples was modified directly in a Zetasizer Nano ZS instrument (20-50° C., with a thermal equilibrium time of 15 min for each measurement of hydrodynamic diameter and zeta potential). For the lyophilization and reconstitution studies, 2 mL of AMT/PSS (0.1% w/v) was frozen at −20° C. with the cryoprotectant trehalose (5% and 10%). The lyophilization procedure was carried out in a freeze-dryer equipment using a high vacuum pump (50 mTorr) for 24 h. The AMT/PSS formulation were reconstituted by adding 2 mL of Milli-Q® water to the freeze-dried powders, followed by manual agitation, before hydrodynamic diameter and zeta potential were analyzed using known protocols.

The determination of nanoparticles concentration was performed in a Nanoparticle Tracking Analyzer. The samples were diluted from 5 to 10 times with Milli-Q water to achieve an optimum concentration range of $10^7$-$10^9$ particles/mL.

Results:

When comparing formulations containing PVS with those containing PSS, there was an absence of turbidity in the former but the presence of turbidity in the latter (FIG. 4). The presence of turbidity between aromatic polyelectrolytes and aromatic low molecular-weight drugs suggests the formation of nanostructures due to the occurrence of additional short-range interactions that strengthen molecular assembling. Thus, ion pairs may be formed due to the short-range character of the interaction, and these ion pairs aggregate forming hydrophobic domains that lead to coacervation.

Nanoparticle formation occurred from drug/PSS ratios of 0.55 to 0.75 (120-170 nm), showing negative zeta potential (−60 to −80 mV). The high zeta potential, which suggests high stability of the formulations and low polydispersity of the particles regarding their size distribution (polydispersity index (PDI) of 0.14-0.19) is of particular note. Interestingly, compositions comprising CBZ/PSS showed a narrower range of turbidity (n+/n−=0.55 to 0.60) compared with AMT/PSS and IMI/PSS (n+/n−=0.60 to 0.75). The results also showed that, as the drug concentration increased, the size of the nanoparticles also tended to increase. The synthesis of the nanoparticles shown here does not need any purification step (after or before combination/mixing).

As seen from the electronic microscopy images of FIG. 5, the nanoparticles have a spheroidal shape and a diameter of about 140 nm.

Figure 6:
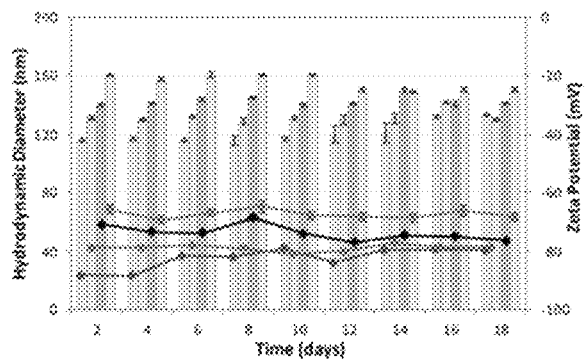
FIG. 6 shows the results of the stability study of AMT/PSS nanoparticles with hydrodynamic diameter (bars) and zeta potential (lines) as a function of time. Left hand bar represents AMT/PSS n+/n−=0.60, second bar represents AMT/PSS n+/n−=0.65, third bar represents AMT/PSS n+/n−=0.70 and right hand bar represents AMT/PSS n+/n−=0.75. (Mean±SD; n=3).

The stability of the nanoparticles was also analyzed. As can be seen in FIG. 6, the hydrodynamic diameter and the zeta potential of AMT/PSS formulations remained practically unchanged at least for 18 days. Similarly, stable size and zeta potential were found in the presence of different salt concentration (FIG. 7A), pH variations (FIG. 7B), and temperature variations (FIG. 7C). In addition, the AMT/PSS formulations were also stable to freeze-drying and reconstitution in water (FIG. 7D). These results indicate that optimal resuspension of the dried product is achieved without altering the hydrodynamic diameter and zeta potential of the original (fresh) formulations.

Figure 8:
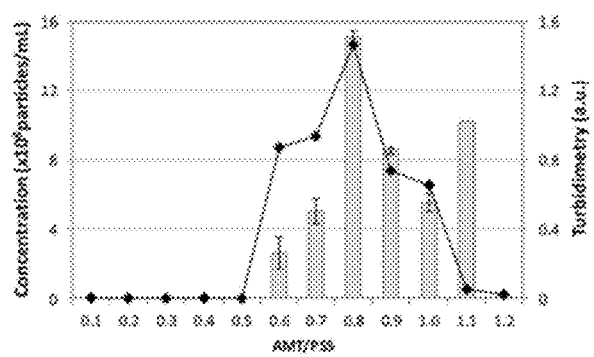
FIG. 8 shows nanoparticle concentration (bars) and turbidimetry (lines) of AMT/PSS formulations (n+/n−=0.1 to 1.0) (Mean±SD, n=3).

In order to study the relation between the concentration of the components and the yield in terms of the number of nanoparticles, the method of nanoparticle tracking analysis (NTA) was used. NTA is a method for visualizing and analyzing particles in liquids that relates the rate of Brownian motion to particle size. The rate of movement is related only to the viscosity and temperature of the liquid; it is not influenced by particle density or refractive index. NTA allows the determination of a size distribution profile of small particles with a diameter of approximately 10-1000 nanometers (nm) in liquid suspension. As can be seen in FIG. 8, the number of formed nanoparticles stood in the range of $2.6 \times 10^8$ and $15.1 \times 10^8$ NPs/mL. Interestingly, a direct relation between the concentration of the nanoparticles and turbidity was observed by spectrophotometry. This is important because, in the absence of nanoparticle tracking analysis (NTA), turbidimetry could also be used to obtain the relative concentration of the nanoparticles.

Figure 7:
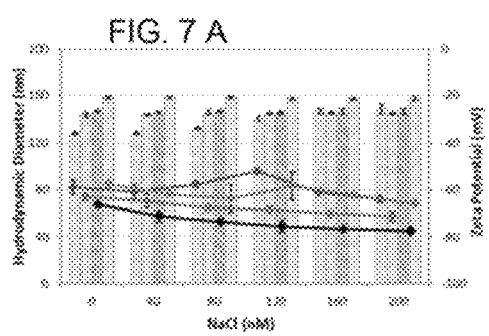
FIG. 7 shows the results of the stability study of AMT/PSS nanoparticles with hydrodynamic diameter (bars) and zeta potential (lines) as a function of different NaCl concentration (FIG. 7A), pH (FIG. 7B), and temperature (FIG. 7C). Hydrodynamic diameter and zeta potential variations for reconstituted freeze-dried AMT/PSS nanoparticles with different concentrations of trehalose (5% and 10%) are shown in FIG. 7D). Left hand bar represents AMT/PSS n+/n−=0.60, send bar represents AMT/PSS n+/n−=0.65, third bar represents AMT/PSS n+/n−=0.70 and right hand bar represents AMT/PSS n+/n−=0.75. (Mean±SD; n=3).
Figure 7:
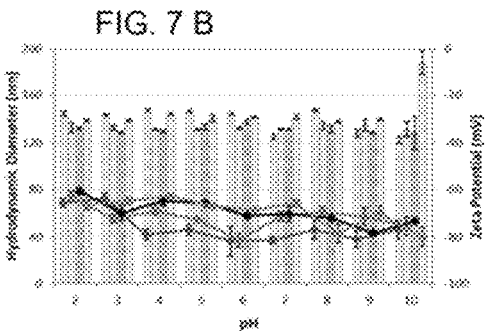
Figure 7:
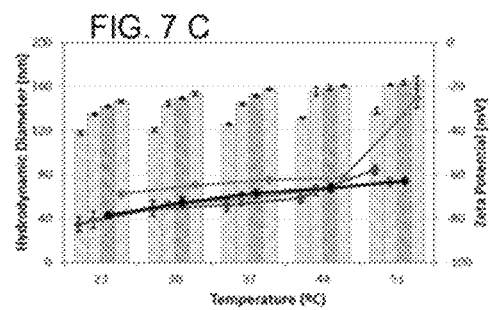
Figure 7:
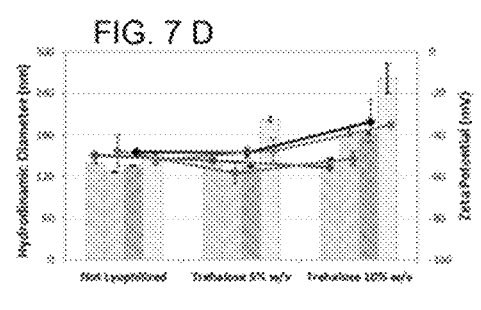

In summary, the nanocarrier composition described herein maintains a hydrodynamic diameter and zeta potential at least for 18 days (FIG. 5). Similarly, stable size and zeta potential was found in the presence of different salt concentration, pHs variations, and temperature variations (FIG. 7). It is important to note that the selected evaluated ranges of salt concentration, pH, and temperature exceed those found in the human body, thus the stability of the nanocarriers is assured. In addition, the compositions have been shown to be stable to freeze-drying and reconstitution in water (FIG. 7). This method is frequently used to preserve the properties of nanoparticle suspensions for storage over extended periods of time. This strategy, due to the total elimination of water, prevents the contamination by microorganisms and facilitates transportation due to the lower weight of the final product. Optimal resuspension of the dried product is achieved without altering the hydrodynamic diameter and zeta potential of the original (fresh) formulations.

Example 2

Diafiltration Studies Using the Nanocarriers Containing HALMD

Diafiltration studies were carried out to determine the fraction of amitriptyline (AMT) that was kinetically or thermodynamically bound to poly(sodium 4-styrenesulfonate (PSS) as the nanoparticle. For this study, diafiltration was been modeled as a two-compartment system, where a continuous liquid supply from the donor chamber (reservoir) is kept, maintaining a constant volume in the diafiltration cell. The unit used for diafiltration analyses consisted of a diafiltration cell, a regenerated cellulose membrane, a reservoir, a selector, and a pressure source. For the diafiltration experiments, aliquots of 10 mL of AMT/PSS formulation were added into the diafiltration cell at an apparent concentration where n+/n−=0.60 to 0.75 and then filtered under 3 bars of pressure with magnetic stirring. The volume in the filtration cell was kept constant during the experiment, by creating a continuous flux of liquid through the diafiltration cell, from the reservoir to the collector tube. Milli-Q water (pH 7) was used as solvent. A total of 8 samples (approx. 5 mL) were collected and AMT concentration in each sample was determined by spectrophotometry.

Subsequently, the thermodynamically bound (TB) and kinetically bound (KB) fractions were determined as follows:

$$TB = v(km-j)/km$$

$$KB = u - um$$

The parameters v and u represent the initial fraction of AMT thermodynamically bound to the particles, thus in equilibrium, and the fraction bound to the nanocarriers whose release is kinetically controlled, respectively. The parameter j is related to the strength of interaction corresponding to the reversibly bound drug fraction (v). The parameters um and km correspond to u and j values, respectively, obtained in blank experiments as control performed by diafiltration of the drug in the absence of other nanocarrier excipients.

Results:

The association efficiency was, in all cases, higher than 90%. Thus, it can be considered that the binding of AMT to the polymer PSS is quantitative. In addition, it is worth highlighting that the drug loading fits in the range of 34-47%. These drug loading values have never been shown with other formulations comprising HALMD (i.e. hydrogels, microgels, polymeric NPs, nanoemulsions, nanocapsules, liposomes, etc.). On the other hand, it can be also seen that the release of AMT is mainly kinetically controlled since more than 80% of the drug molecules were not subjected to equilibrium with the bulk.

TABLE 1

Results for Diafiltration for the AMT/PSS formulations (Mean ± SD, n = 3).

| AMT/PSS | u | v | j | $u^m$ | $k^m$ |
|---|---|---|---|---|---|
| 0.60 | 0.92 ± 0.07 | 0.08 ± 0.06 | 0.37 ± 0.17 | −0.01 | 1.05 |
| 0.65 | 0.87 ± 0.01 | 0.13 ± 0.01 | 0.29 ± 0.01 | 0.06 | 1.00 |
| 0.70 | 0.89 ± 0.11 | 0.11 ± 0.09 | 0.47± 0.02 | 0.05 | 1.01 |
| 0.75 | 0.87 ± 0.01 | 0.13 ± 0.01 | 0.43 ± 0.02 | −0.02 | 1.10 |

In the present invention, the drug is a structural component of the nanoparticle, whose release provides a concomitant detachment of the polymer, thereby exposing the subjacent material (previously subjected to kinetic interaction) to the external environment and promoting the drug release by thermodynamic equilibrium.

Example 3

In Vitro Release

The in vitro drug release of amitriptyline (AMT) from poly (sodium 4-styrenesulfonate (PSS) was evaluated using a dialysis method. Briefly, 5 mL of AMT/PSS (n+/n−=0.60) was transferred to a dialysis membrane. The membrane was immersed in 95 mL of Milli-Q water at pH 7 and kept at 37°

C. and 100 rpm in an orbital shaker. The experiment was carried out for 20 days. Aliquots (500 μL) of the solution were withdrawn at certain time intervals and replaced with an equal volume of fresh Milli-Q water. The amount of released AMT was determined by measuring the absorbance of each aliquot at 239 nm. The standard curve of AMT in water was linear ($R2>0.997$) in the range of concentrations between $7\times10^{-5}$ M and $7\times10^{-7}$ M (molar extinction coefficient was 12712 $M^{-1}$ $cm^{-1}$). Blank experiments dialyzing free AMT were carried out at the same conditions.

Figure 9:
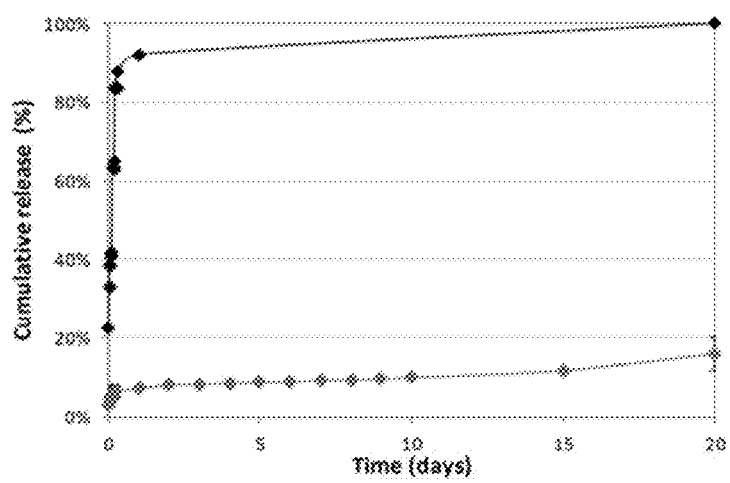
FIG. 9 shows in vitro release of AMT from AMT/PSS formulations (grey line) vs free AMT (black line) (Mean±SD, n=3).

Results:

The in vitro release assays analyzed by dialysis (pH=7 and 37° C.) showed a slow and sustained release of AMT that does not exceed 16.5% in 20 days (FIG. 9). This result suggests that the fraction of AMT released corresponds to the AMT thermodynamically bound to the nanocarrier (5.9%-8.8%, determined by diafiltration). Considering that the drug is a structural component of the nanocarrier, this release would provide a concomitant detachment of the polymer, exposing the subjacent material (previously subjected to kinetic interactions) to the external environment and presumably promoting a prolonged drug release by thermodynamic equilibrium.

Example 4

Characterization and In Vitro Release Studies for Chloroquine (CQ), Promethazine (PMZ) and Chlorphenamine (CPM)

These selected HALMD/PSS formulations were synthetized similarly as described in Example 1. Briefly, 5.0 mL of an aqueous solution containing one cationic HALMD (CQ, PMZ or CPM) was added to 5.0 mL of an aqueous solution containing the anionic polymer (PSS or PVS), both at pH 7, and exposed to continuous stirring (5 min). The formation (or not) of NPs was evidenced through dynamic light scattering (DLS).

NMR analyses were performed in D2O on an Avance400 (Bruker, USA) using glass tubes of 5 mm diameter (volume of solution typically 0.7 mL). Appropriate conditions for 1H-NMR experiments were chosen as [HALMD]=$1\times10^{-3}$ M and [PSS]=$1\times10^{-2}$ M, a volume of 750 μL of each compound was lyophilized individually and reconstituted in $D_2O$ before analysis.

The presence of dispersed particles in aqueous medium was initially analyzed by turbidimetry in an Agilent 8453 spectrophotometer (Agilent, USA), measuring the absorbance of the formulations at a wavelength where none of the compounds (drug and polymer) absorb ($\lambda$=650 nm).

The hydrodynamic diameter and zeta potential of the formulations were determined by dynamic light scattering (DLS) and laser Doppler anemometry (LDA) using a Zeta-Sizer NanoZS (Malvern Instruments, UK).

The determination of nanoparticle concentration was performed in a NanoSight NS300 (Malvern Instruments, UK). The samples were diluted from 5 to 10 times with Milli-Q water to achieve an optimum concentration range of 107-109 particles/mL. A minimum of five videos (one minute each one) of the particles moving under Brownian motion were captured by the NanoSight. The videos were then analyzed for size distribution and particle concentration using the built-in NTA v 3.0 software (Malvern, UK).

The morphological characterization was carried out in a scanning transmission electron microscope (STEM), model Inspect F-50 (FEI, Holland). STEM images were obtained by sticking a droplet (20 μL) of the formulation to a copper grid (200 mesh, covered with Formvar) for 2 min, then removing the droplet with filter paper avoiding the paper touching the grid, then washing the grid twice with a droplet of Milli-Q water for 1 min and removing the droplet with filter paper. Subsequently, the sample was stained with a solution of 1% (w/v) phosphotungstic acid by adding a droplet of this solution to the grid for 2 min and then removing with filter paper. Finally, the grid was dried at room temperature for at least 1 h before being analyzed.

The association efficiency of HALMD in the nanoparticles was determined by analyzing the ratio between the amount of drug associated in the formulation and the total initial drug (associated and non-associated). The drug loading (% w/w) was calculated by dividing the amount of drug associated in the formulation by the total weight of the nanoparticles. The yield was calculated by dividing the total weight of NPs by the total weight of the components in the feed for each formulation (drug+PSS). The drug content into the nanoparticles was calculated indirectly by quantifying the free drug in the medium; the separation of nanoparticles and free drug was done by using Vivaspin®6 tubes (MWCO 3 KDa, 5000 G×40 min). The quantification of the CQ, PMZ, and CPM was done by measuring the absorbance at 220 nm, 250 nm and 262 nm (Agilent 8453 spectrophotometer, USA), respectively. The standard curve of CQ was linear ($R2>0.999$) in the range of concentrations between $4\times10^{-5}$ M and $3\times10^{-6}$ M (molar extinction coefficient was 30449 $M^{-1}$ $cm^{-1}$). The standard curve of PMZ was linear ($R2>0.999$) in the range of concentrations between $3.5\times10^{-5}$ M and $5\times10^{-6}$ M (molar extinction coefficient was 24921 $M^{-1}$ $cm^{-1}$). The standard curve of CPM was linear ($R2>0.999$) in the range of concentrations between $1.4\times10^{-4}$ M and $2\times10^{-5}$ M (molar extinction coefficient was 5781 M−1 cm-1). Finally, for the calculation of the total weight of the nanoparticles, 1 mL of each formulation was lyophilized in glass vials, which were weighed before adding the formulation and after freeze-drying to assess the total solid mass (glass vials+formulation). The lyophilization procedure was done in the freeze-dryer equipment FreeZone 1 (Labconco, USA) using a high vacuum pump (50 mTorr) for 24 h.

The diafiltration method was selected to investigate the kinetic and/or thermodynamic drug entrapment, and the dissociation constants to excipients and formulations dispersed in aqueous medium, following a procedure similar to the described in Example 2. The method consists on a two-compartment system, where a continuous liquid supply from the donor chamber (reservoir) is kept, maintaining a constant volume in the diafiltration cell. The unit used for diafiltration analyses consisted of a diafiltration cell (10 mL, Amicon 8010), a regenerated cellulose membrane (cutoff of 5000 Dalton, Merck, Germany), a reservoir, a selector, and a pressure source (Merck-Millipore, Germany). For the diafiltration experiments, aliquots of 10 mL of the formulations were added into the diafiltration cell and then filtered under 3 bars of pressure and magnetic stirring. The volume in the filtration cell was kept constant during the experiment, by creating a continuous flux of liquid through the diafiltration cell, from the reservoir to the collector tube. Milli-Q water (pH 7) was used as solvent. A total of 8 samples (approx. 5 mL) were collected and the concentration of the interest species in each sample was determined by spectrophotometry.

Also, the diafiltration was performed to determine the fraction of HALMD (CQ, PMZ and CPM) kinetically or thermodynamically bound to PSS. Details of diafiltration procedures, mathematical analysis and results are described in Example 2.

In-vitro release assays were carried out using two different methods: i) conventional dialysis and ii) USP apparatus 4 (continuous flow-cell).

i) Dialysis: 5 mL of HALMD/PSS formulations were added in a dialysis bag (MWCO 10 kDa, ThermoScientific, USA). The dialysis system was immersed in 95 mL of Milli-Q water at pH 7 and kept at 37° C., and 100 rpm in an orbital shaker (LSI-3016R, LabTech, Daihan LabTech, Kyonggi-Do, Korea). The experiment was carried out for 20 days, aliquots (500 µL) of the solution were withdrawn at certain time intervals and replaced with an equal volume of fresh Milli-Q water. The amount of released HALMD (CQ, PMZ and CPM) was determined by measuring the absorbance of each aliquot by spectrophotometry (Agilent 8453 spectrophotometer, USA).

ii) USP apparatus 4: For this assay, the set-up of the continuous flow method is combined with a dialysis membrane to contain the nanoformulations into the cell. In brief, 5 mL of HALMD/PSS formulations were added in a dialysis bag (MWCO 10 kDa, ThermoScientific, USA) and then immersed into the flow-cell (12.5 mL capacity). Drug release studies were assessed using 250 mL of Milli-Q water at pH 7. The continuous flow-cell (Sotax CE 6, Sotax AG, Switzerland) is operated in close configuration at 37° C. and with a flow rate of 4 mL/min approximately. The experiment was carried out for 6 hours, aliquots (500 µL) of the solution were withdrawn every 30 min and replaced with an equal volume of fresh Milli-Q water. The amount of released HALMD (CQ, PMZ and CPM) was determined by measuring the absorbance of each aliquot by spectrophotometry (Agilent 8453 spectrophotometer, USA). To investigate the release mechanism (in both conventional dialysis and the USP apparatus 4 data), mathematical kinetics modelling was analysed using the program DDSolver. The coefficient of determination (R2), the Akaike information criteria (AIC), and the model selection criteria (MSC) parameters were considered for the model selection. Finally, the release data was fitted to zero order, first order, Higuchi and Korsmeyer-Peppas.

Figure 10:
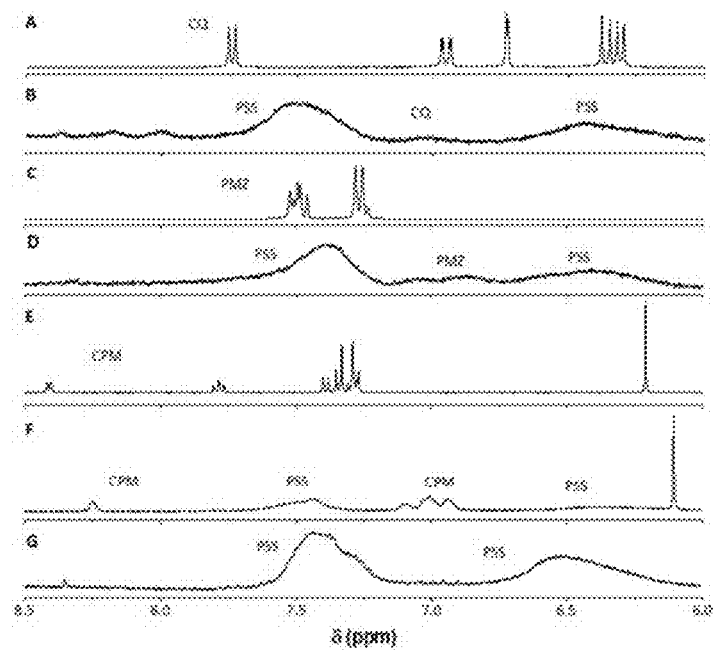
FIG. 10 shows the $^1$H-NMR spectra (500 MHz) in $D_2O$ at pH 7 of the aromatic region of samples containing: CQ $1\times10^{-3}$ M in the absence of PSS (A), CQ $1\times10^{-3}$ M in the presence of PSS $1\times10^{-2}$ M (B), PMZ $1\times10^{-3}$ M in the absence of PSS (C), PMZ $1\times10^{-3}$ M in the presence of PSS $1\times10^{-2}$ M (D), CPM $1\times10^{-3}$ M in the absence of PSS (E), CPM $1\times10^{-3}$ M in the presence of PSS $1\times10^{-2}$ M (F) and PSS $1\times10^{-2}$ M (G).

Results:

The $^1$H-NMR experiments demonstrated strong shifting of HALMD aromatic signals in the presence of the polymer PSS, evidencing intimate interactions between the structures, attributed to aromatic-aromatic interactions. The FIG. 10 shows that the signals corresponding to aromatic protons (between 6.0 and 8.0 ppm) of tested HALMD are upfield shifted in the presence of PSS, evidencing close proximity between the benzenesulfonate groups from PSS and the aromatic region of the HALMD.

Figure 11:
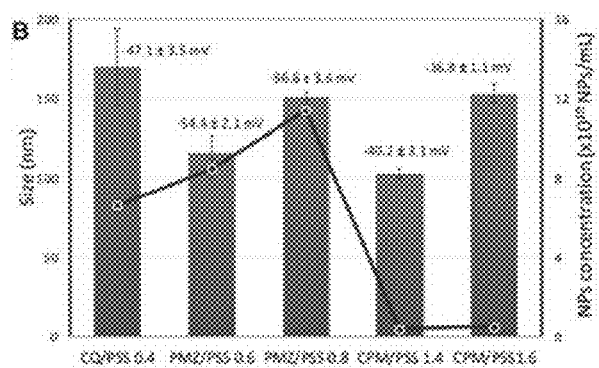
FIG. 11 shows the size of NPs (bars), number of NPs (NPs/mL) (lines) and zeta potential (number) of HALMD/PSS NPs (Mean±SD; n=3).

Although the selected HALMD share important characteristics in terms of functional groups (tertiary amines), polarizability, pKa, and log P (as shown in Table 2), the number of formed NPs is significantly higher for HALMD showing lower critical aggregation concentration (CQ and PMZ, FIG. 11), even though a much lower concentration of the drug (between 200 to 400% lesser drug concentration) and polymer (50% lesser polymer concentration) is present, strongly supporting the crucial role of the self-aggregation tendency of the drugs in the feasibility of obtaining nanomedicines. Finally, analyses by electronic microscopy images obtained by STEM revealed spherical and reproducible NPs independently of the selected drug and/or charge ratio formulation.

TABLE 2

Some physicochemical properties of the tested HALMD

| HALMD | pK$_a$ | Polarizability (Å$^3$) | Theorical partition coefficient (log P) | Critical aggregation concentration (cac) (mM) |
|---|---|---|---|---|
| Chloroquine | 8.4, 10.3 | 38.08 | 3.93 | 10 |
| Promethazine | 9.1 | 34.15 | 4.29 | 36 |
| Chlorpheniramine | 4.0, 9.4 | 31.55 | 3.58 | 69.5 |

As shown in Table 3, the association efficiency for selected HALMD are high and stood in the range of 80 to 100% evidencing the effectiveness of the process in terms of the entrapment of HALMD. Here, the NPs achieved drug loading values up to 67% which is largely higher compared with other strategies in the previous art involving the encapsulation of HALMD in NPs (1.3-27.2%). Additionally, the yield (reflecting of mass of obtained product versus the initial mass of the components) is also very high for all tested formulations (up to 94%) evidencing the success of the present invention.

The association efficiency was, in all cases, higher than 80%. In Table 3 is shown that in the case of the molecules with lower critical aggregation concentration (CQ and PMZ) the drug association is almost fully attributed to kinetic binding (≥90%), while a lower fraction of CPM, which show a larger critical aggregation concentration, is subjected to kinetical entrapped (≈50%). The self-association tendency of the drugs also impacts the dissociation constant observed for the thermodynamically bound fraction of drugs.

TABLE 3

Association parameters of HALMD/PSS NPs (Mean ± SD, n = 3)

| HALMD/PSS (n+/n−) | Association Efficiency (%) | Drug Loading (%) | Yield (%) |
|---|---|---|---|
| CQ/PSS (0.4) | 99.8 ± 0.1 | 48.6 ± 4.1 | 88.8 ± 16.5 |
| PMZ/PSS (0.6) | 97.5 ± 0.3 | 50.7 ± 2.8 | 90.6 ± 4.6 |
| PMZ/PSS (0.8) | 95.6 ± 0.9 | 53.0 ± 5.5 | 81.4 ± 10.0 |
| CPM/PSS (1.4) | 82.7 ± 2.6 | 59.4 ± 1.0 | 93.7 ± 3.9 |
| CPM/PSS (1.6) | 88.3 ± 1.0 | 67.2 ± 0.4 | 94.0 ± 6.3 |

Figure 12:
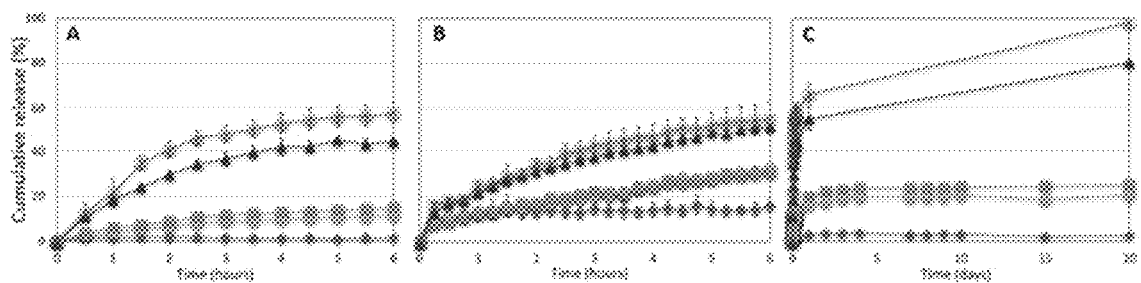
FIG. 12 shows the in vitro release profiles at pH 7.0 (37° C.) of formulations containing CQ/PSS 0.4 (◇); PMZ/PSS 0.6 (●), PMZ/PSS 0.8 (□); CPM/PSS 1.4 (Δ) and CPM/PSS 1.6 (x) by conventional dialysis (A) and USP 4 apparatus (B) for a period time of 6 hours, and dialysis during 20 days (C) (Mean±SD, n=3).

The release studies performed show (FIG. 12) that the selected molecules exhibited significant differences in the drug release profiles during the first 6 h (CQ/PSS 0.4≈1.5%, PMZ/PSS 0.6≈11.5%, PMZ/PSS 0.8≈15%, CPM/PSS 1.4≈44.3% and CPM/PSS 1.6≈57.6%). As can be seen in FIG. 12B, the releases profiles are similar to those obtained by dialysis, showing higher release for HALMD with the highest critical aggregation concentration (CQ/PSS 0.4≈16.2%, PMZ/PSS 0.6≈32.8%, PMZ/PSS 0.8≈30.5%, CPM/PSS 1.4≈51.5% and CPM/PSS 1.6≈55.7%). FIG. 12C evidenced a drug release profile (dialysis) for a longer period (20 days). Concordantly with our previous proposal, the most prolonged drug delivery was achieved for those HALMD with lower cac (CQ/PSS 0.4≈2.6%, PMZ/PSS 0.6≈20.5% and PMZ/PSS 0.8≈25%) while a significantly faster release was obtained for CPM (CPM/PSS 1.4≈80.0% and CPM/PSS 1.6≈98.0%).

In general, the release profile and the high drug loading values conceptually respond to an innovative approach: the drug, besides being the functional molecule to be carried by the nanoparticle, constitutes a key structural component of the nanoparticle. The dual function of the drugs in this system arises from the occurrence of short-range aromatic-aromatic interactions, producing ion pairs, with release of water from the respective hydration shells of both interacting components. The components then tend to aggregate and migrate to the inner polymeric hydrophobic environment, allowing the collapse of the system in the form of nanoparticles.

All publications mentioned in the above specification are herein incorporated by reference. Various modifications and variations of the described methods and compositions of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A nanocarrier composition for formulating a hydrophilic and aromatic low molecular-weight drug (HALMD), the composition comprising:
    an aromatic polymer selected from poly(sodium 4-styrenesulfonate) (PSS), hypromellose phthalate, and derivatives thereof; and
    a hydrophilic and aromatic low molecular-weight drug (HALMD);
    wherein the hydrophilic and aromatic low molecular-weight drug (HALMD) comprises a tertiary amine and an aromatic group.

2. The nanocarrier composition according to claim 1, wherein the HALMD is selected from imipramine, cyclobenzaprine, amitriptyline, amoxapine, desipramine, doxepin, nortriptyline, protriptyline, trimipramine, atenolol, metoprolol, propranolol, amlodipine, doxorubicin, paroxetine, venlafaxine, levodopa, carbinoxamine, clemastine, dimenhydrinate, diphenhydramine, doxylamine, pyrilamine, tripelennamine, chloropyramine, chlorpheniramine, brompheniramine, cyproheptadine, hydroxyzine, ciclizine, meclizine, promethazine, acrivastine, cetirizine, terfenadine, astemizole, levocabastine, loratadine, azatadine, phenindamine, diphenylpyraline, ebastine, levocetirizine, fexofenadine, desloratadine, tecastemizole, chloroquine, hydroxychloroquine, amodiaquine, mefloquine, and derivatives thereof.

3. The nanocarrier composition according to claim 1, wherein the composition has a drug loading value from 30 to 100%.

4. The nanocarrier composition according to claim 1, wherein the composition has a size of between 50 and 400 nm.

5. The nanocarrier composition according to claim 1, wherein the composition has a zeta potential from +100 to −100 mV.

6. The nanocarrier composition according to claim 1, wherein the aromatic polymer and the HALMD are present in the composition in a concentration such that a final apparent concentration is defined according to following formula:

$$[\text{final apparent concentration}] = \frac{n+}{n-}$$

wherein n+ is a molar concentration of a cationic aqueous solution and n− is a molar concentration of an anionic aqueous solution.

7. The nanocarrier composition according to claim 6, wherein the final apparent concentration is between 0.1 and 1.6.

8. A pharmaceutical composition comprising the nanocarrier composition of claim 1, optionally, one or more physiologically or pharmaceutically acceptable carriers, excipients and/or diluents.

* * * * *